US010214747B2

(12) United States Patent
Morton et al.

(10) Patent No.: US 10,214,747 B2
(45) Date of Patent: Feb. 26, 2019

(54) METHOD OF PURIFYING MONOCLONAL ANTIBODIES

(71) Applicant: Kentucky BioProcessing, Inc., Winston-Salem, NC (US)

(72) Inventors: Josh Morton, Evansville, IN (US); Barry Bratcher, Owensboro, KY (US); Kelsi Swope, Maceo, KY (US); Emmett Ernest Hiatt, III, Maceo, KY (US); Steven D. Hume, Owensboro, KY (US); Larry Zeitlin, Poway, CA (US)

(73) Assignee: KENTUCKY BIOPROCESSING, INC., Winston-Salem, NC (US)

( * ) Notice: Subject to any disclaimer, the term of this patent is extended or adjusted under 35 U.S.C. 154(b) by 0 days.

(21) Appl. No.: 15/110,200

(22) PCT Filed: Oct. 3, 2014

(86) PCT No.: PCT/US2014/059159
§ 371 (c)(1),
(2) Date: Jul. 7, 2016

(87) PCT Pub. No.: WO2015/105551
PCT Pub. Date: Jul. 16, 2015

(65) Prior Publication Data
US 2016/0333365 A1    Nov. 17, 2016

Related U.S. Application Data

(60) Provisional application No. 61/925,580, filed on Jan. 9, 2014.

(51) Int. Cl.
| | |
|---|---|
| *C07K 1/36* | (2006.01) |
| *B01D 15/38* | (2006.01) |
| *C07K 16/00* | (2006.01) |
| *C07K 16/06* | (2006.01) |
| *C07K 16/16* | (2006.01) |
| *C12N 15/82* | (2006.01) |
| *C07K 16/10* | (2006.01) |
| *C07K 16/12* | (2006.01) |
| *C07K 16/32* | (2006.01) |

(52) U.S. Cl.
CPC ..... *C12N 15/8258* (2013.01); *B01D 15/3809* (2013.01); *C07K 1/36* (2013.01); *C07K 16/00* (2013.01); *C07K 16/065* (2013.01); *C07K 16/10* (2013.01); *C07K 16/1271* (2013.01); *C07K 16/16* (2013.01); *C07K 16/32* (2013.01); *C07K 2317/13* (2013.01); *C07K 2317/33* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,177,548 B1 * | 1/2001 | Wan | C07K 16/065 530/390.1 |
| 8,278,065 B2 * | 10/2012 | Nicolaides | C07K 16/3084 435/252.3 |
| 2009/0041776 A1 | 2/2009 | Koprowski et al. | |
| 2010/0234577 A1 * | 9/2010 | Mazzola | C07K 1/18 530/388.1 |
| 2012/0208986 A1 * | 8/2012 | Wenger | B01D 15/327 530/388.4 |
| 2012/0237532 A1 | 9/2012 | Olbrich et al. | |
| 2016/0083453 A1 * | 3/2016 | Hunter | C07K 16/065 530/387.3 |

FOREIGN PATENT DOCUMENTS

| | | |
|---|---|---|
| EP | 1029064 B1 | 5/2006 |
| WO | 9924592 A1 | 5/1999 |
| WO | 2006040764 A2 | 4/2006 |
| WO | 2006040764 A3 | 4/2006 |
| WO | 2011150110 A1 | 12/2011 |

(Continued)

OTHER PUBLICATIONS

U.S. Department of Health and Human Services "Points to Consider in the manufacture and testing of monoclonal antibody products for human use" pp. 1-50 (Year: 1997).*
The United States Patent and Trademark Office; The International Search Report and Written Opinion; International Search Report and Written Opinion for PCT/US2014/059159; dated Jan. 14, 2015; The United States Patent and Trademark Office; U.S.
Villani, et al.; Plant pharming of a full-sized, tumour-targeting antibody using different expression strategies; Journal article; pp. 59-72; Plant Biotechnology Journal; 2009; vol. 7; doi: 10.1111/j.1467-7652.2008.00371.X; © 2008 The Authors; Journal compilation © 2008 Blackwell Publishing Ltd.
Charles J. Arntzen; Molecular Pharming in Plants—a disruptive technology for the mammalian production based pharma sector?; The biodesign Institute; Arizona State University Center for Infectious Diseases and Vaccinology; Molecular Pharming Symposium; ABIC 2008; pp. 1-23; charles.arntzen@asu.edu; Cork, Ireland.

(Continued)

*Primary Examiner* — Daniel E Kolker
*Assistant Examiner* — James L Rogers
(74) *Attorney, Agent, or Firm* — Wyatt, Tarrant & Combs, LLP; Stephen C. Hall; Max E. Bridges

(57) ABSTRACT

A new platform method to purify plant-based monoclonal antibodies is provided. Such a method includes an antibody purification platform that involves a standardized procedure for the production of a wide array of different antibodies within a simplified context. The versatility of the overall purification process accords a one-size-fits-all approach for myriad antibody products and includes plant tissue harvesting, extraction and clarification, filtrate generation, a succession of column chromatography procedures, and buffer exposure to provide the desired monoclonal antibodies in proper filtered and purified form for further incorporation and/or use within medicaments and other formulations. Thus, the purified monoclonal antibodies produced thereby such a method are also encompassed within this invention.

10 Claims, 8 Drawing Sheets

(56) References Cited

FOREIGN PATENT DOCUMENTS

| WO | 2013066707 A1 | 5/2013 |
| WO | 2013165732 A1 | 11/2013 |

OTHER PUBLICATIONS

Husk, et al.; Monoclonal Antibody Purification (*Nicotiana benthamiana* Plants); bio-protocol; article; Jan. 20, 2014; pp. 1-6; vol. 4; Issue 2; http:...www.bio-protocol.org/e1034.

James Pettitt, et al.; Therapeutic Intervention of Ebola Virus Infection in Rhesus Macaques with the MB-003 Monoclonal Antibody Cocktail; Research Article; Aug. 21, 2013; pp. 1-6; 5(199): 199ra113; www. ScienceTranslationalMedicine.org.

Zeitlin, et al.; Prophylactic and therapeutic testing of Nicotiana-derived RSV-neutralizing human monoclonal antibodies in the cotton rat model; Report; Mar./Apr. 2013; pp. 263-269; mAbs 5:2; © 2013 Landes Bioscience; www.landesbioscience.com.

Karauzum, et al.; Synthetic Human Monoclonal Antibodies toward Staphylococcal Enterotoxin B (SEB) Protective against Toxic Shock Syndrome; Journal Article; The Journal of Biological Chemistry; Jul. 20, 2012; pp. 25203-25215; vol. 287, No. 30; © 2012 by The American Society for Biochemistry Molecular Biology, Inc. Published in the U.S.A.

Whaley, et al.; Antibody-based concepts for multipurpose prevention technologies; Journal article; Antiviral Research; 2013; pp. S48-S53; 100; journal homepage: www.elsevier.com/locate/antiviral; http://www.sciencedirect.com; © 2013 Elsevier B.V.

Olinger, Jr., et al.; Delayed treatment of Ebola virus infection with plant-derived monoclonal antibodies provides protection in rhesus macaques; Article; PNAS; Oct. 30, 2012; pp. 18030-18035; vol. 109, No. 44; www.pnas.org/cgi/doi/10.1073/pnas.1213709109.

Pogue, et al.; Production of pharmaceutical-grade recombinant aprotinin and a monoclonal antibody product using plant-based transient expression systems; Journal article; 2010; Plant Biotechnology Journal; pp. 638-654; 8; doi: 10.1111/j.1467-7652.2009.00495.x; © 2010 The Authors; Journal compilation; © 2010 Blackwell Publishing Ltd.

Hiatt, et al.; Glycan variants of a respiratory syncytial virus antibody with enhanced effector function and in vivo efficacy; Article; PNAS; Apr. 22, 2014; pp. 5992-5997; vol. 111; No. 16; www.pnas.org/cgi/doi/10.1073/pnas.1402458111.

Sully, et al.; Chimeric Plantibody Passively Protects Mice against Aerosolized Ricin Challenge; Article; Clinical and Vaccine immunology; May 2014; pp. 777-782; vol. 21; No. 5; cvi.asm.org.

Sully, et al.; A tripartite cocktail of chimeric monoclonal antibodies passively protects mice against ricin, staphylococcal enterotoxin B and Clostridium perfringens epsilon toxin; Journal article; 2014; pp. 36-41; Toxicon 92; journal homepage: www.elsevier.com/locate/antiviral; http://www.sciencedirect.com; © 2014 Elsevier Ltd.

Hamorsky, et al.; Efficient Single Tobamoviral Vector-Based Bioproduction of Broadly Neutralizing Anti-HIV-1 Monoclonal Antibody VRC01 in *Nicotiana benthamiana* Plants and Utility of VRC01 in Combination Microbicides; Journal article; Antimicrobial Agents and Chemotherapy; May 2013; pp. 2076-2086; vol. 57, No. 5; www.aac.asm.org; JournalsASM.org.

Chen; Expression and Purification of Pharmaceutical Proteins in Plants; article; Biological Engineering; Jan. 2008; pp. 291-321; vol. 1, No. 4; https://www.researchgate.net/publication/215643480.

Liu, et al.; Recovery and purification process development for monoclonal antibody production; article; mAbs; Sep./Oct. 2010; pp. 480-499, vol. 2, issue 5; © 2010 Landes Bioscience; www.landesbioscience.com.

Shukla, et al.; Downstream processing of monoclonal antibodies—Application of platform approaches; Journal article; Journal of Chromatography B; 2007; pp. 28-39; vol. 848; © 2006 Elsevier B.V.;www.sciencedirect.com;www.elsevier.com/locate/chromb.

McClean, et al.; Purification of the therapeutic antibody trastuzumab from genetically modified plants using safflower Protein A-oleosin oilbody technology; paper; Transgenic Res; 2012; pp. 1291-1301; vol. 21; © Springer Science+Business media B.V. 2012.

Pegel, et al.; Evaluating Disposable Depth Filtration Platforms for MAb Harvest Clarification; article; Bioprocess International; Oct. 2011; pp. 52, 54-55 (the original article was published without mention of p. 53); vol. 9, issue 9; www.bioprocessintl.com.

Low, et al.; Future of antibody purification; article; Journal of Chromatography B; 2007; pp. 48-63; © 2006 Elsevier B.V.;www.sciencedirect.com; www.elsevier.com/locate/chromb.

Giritch, et al.; Rapid high-yield expression of full-size IgG anitbodies in plants coinfected with noncompeting viral vectors; article; PNAS; Oct. 3, 2006; pp. 14701-14706; vol. 103; No. 40; www.pnas.org; © 2006 by the National Academy of Sciences of the USA.

Stein, et al.; The regulation of biologic products derived from bioengineered plants; opinion; Biotechnology; 2001; pp. 308-311; vol. 12; www.elsevier.com.

* cited by examiner

Antibody D

METHOD OF PURIFYING MONOCLONAL ANTIBODIES

CROSS-REFERENCE TO RELATED APPLICATIONS

This national stage patent application, filed under 35 U.S.C. § 371, claims priority to PCT Patent Application No. PCT/US14/59159, filed on 3 Oct. 2014, which claims priority to U.S. Provisional Patent Application No. 61/925,580, filed on 9 Jan. 2014.

FIELD OF THE INVENTION

The present invention is directed to a new method to purify plant-based monoclonal antibodies. Such a method includes an antibody purification platform that involves a standardized procedure for the production of a wide array of different antibodies within a simplified context. The versatility of the overall purification process accords a one-size-fits-all approach for myriad antibody products and includes plant tissue harvesting, extraction and clarification, filtrate generation, a succession of column chromatography procedures, and buffer exposure to provide the desired monoclonal antibodies in proper filtered and purified form for further incorporation and/or use within medicaments and other formulations. Thus, the purified monoclonal antibodies produced by such a method are also encompassed within this invention.

BACKGROUND OF THE INVENTION

Monoclonal antibodies have been used within the medical field, at least, for many years, particularly as a means to permit binding to specific antigens within an organism. In such a manner, such antibodies can be created to target certain types of cells to promote any type of response, primarily deactivation, detection, and/or purification of substances.

Generally speaking, monoclonal antibodies are structures that are substantially the same in composition and form that are made by identical immune cells, being, in essence, and as their name implies, clones of a unique parent cell. Thus, these antibodies exhibit monovalent affinity for the same target epitope, permitting a rather large-scale (at a microscopic level) potential platform to effectively treat certain infectious (or other like) substances within an organism. As such, it has been realized that it is possible to produce monoclonal antibodies that can be engineered to actually bind to any given substance. Thus, monoclonal antibodies have been long utilized as important tools to provide effective targeted treatments, medically and otherwise, for undesirable in vivo substances.

The general method of monoclonal antibody production is well known. However, in order to properly provide a suitable medicament, etc., including such biochemical structures, one must first ensure that the antibodies themselves do not include extraneous substances themselves that could prove deleterious to the target organism (or even possibly counteract the effectiveness of the antibodies during application). For instance, the potential for harmful mammalian virus transfer through the utilization of animal cells (such as CHO, NSO, Per-C6, as examples) for such a purpose, as well as the relatively large cost of such testing protocols certainly give pause as to the continued implementation of such mammalian-based monoclonal antibody harvesting. Such residual virus particles, herein defined as materials that are capable of initiating an infection within a mammalian cell, require a number of actions to ensure utility of such antibodies subsequent to actual production. For instance, inactivation of the virus strains themselves are required to provide reliable results (since total removal from such produced materials may not be achieved or, alternatively, active viruses may deleterious effect the production method itself). Such necessary inactivation and removal steps are to the overall complexity and costs of mammalian-based antibody production schemes. Avoidance of these added steps and potential problems are of great importance to allow for more streamlined antibody production capabilities, certainly.

Otherwise, there still exists the necessity to purify such resultant structures, leaving as close to just the desired specific monoclonal antibody constructs alone. There are a wide variety of purification techniques that have been developed for this purpose, with each procedure seemingly directed to highly specific antibody structures, as opposed to the potential for purification processes for a wide variety of antibodies. Although the specific methods that have been employed may be effective for such individualized antibody structures, unfortunately these unique procedures are not cost-effective as there are very few locations and companies that center on a single monoclonal antibody production scheme. To the contrary, typically multiple antibody formulations are produced at the same place, thus requiring not only divergent starting materials and controls in that respect, but also the required undertaking of shifting purifying methods at great expense in order to target such specific end results. There thus exists a significant need to provide not only an effective all-encompassing purification method for monoclonal antibody production purposes, but also a need to provide such a purification platform that accords a reliable method in that respect that guarantees, to a certain degree, at least, that the resultant antibodies will exhibit optimal activity levels for their intended use. To date, such a one-size-fits-all approach for antibody production and purification has been natively absent within the biochemical and medical fields.

Certainly, as alluded to above, there have been a wide variety of general purification methods for antibodies. However, again, such techniques are not directed to the potential to provide an overarching purification platform for different types and potentially different classes of monoclonal antibodies. Additionally, many such targeted purification schemes are developed to achieve such ends with minimal processing steps, rather than from a view that standardized procedures may accord greater efficiencies in the long run. As well, these specific purification protocols require the utilization of different reagents, buffers, etc., compounds and formulations that further necessitate additional testing and regulatory compliance if involving antibodies for human ingestion/introduction at some point. Thus, although such "quick" methods may provide effective purification results for specific monoclonal antibody products, in actuality, the overall costs to achieve not just development success, but regulatory compliance, ultimately, militates against such actions.

Additionally, traditional antibody production methods have typically involved a specific fingerprint process for each specific type of compound involved. In essence, a targeted antibody has required a specific production and purification protocol that concerns optimum levels for that specific antibody alone. Thus, if a new antibody were produced, or at least developmental activities were devoted to a specific type or types, in the past the overall provision for such an antibody required a narrow and specific method to generate a threshold amount for testing and ultimate implementation purposes. Such unique fingerprint steps undertaken for antibody generation thus limited efforts in terms of scalability; the requirement that specific methodologies be followed with little to no deviation led to higher potentials for compromised production batches (slight modifications from set protocols could lead to failure in terms of effective results). Thus, there exists a definite need to provide a more uniform, if not a one-size-fits-all approach, to antibody production methods. To date, such has simply not been made available, whether in terms of mammalian-based processes or otherwise.

Of particular interest and appeal in terms of the utilization of monoclonal antibodies (mAbs) for numerous therapeutic and prophylactic treatments (for mammalian subjects, at least) are the potency, specificity, and safety profile of these materials. However, as alluded to above, there are serious challenges involved in the production and development of new mAb products, particularly as it concerns reliable and consistent manufacturing procedures and results. For example, the potential growth and spread of diseases, whether through natural or human-inflicted (e.g., WMD) consequences requires scalability for quick and effective supply of medical treatments utilizing such platforms. In essence, with the number of diseases growing, rather than shrinking, worldwide, larger quantities of mAbs are necessary to meet expected and unexpected disease activities in order to provide for disease protection and treatment. Even moderate production levels may be sufficient for individuals that are subjected to locations prone to exposure to viruses and other weapon-based (for instance) situations, particularly in at-risk areas or for clinical trial applications. Reliability and efficiency, though, will still be paramount in order to properly accord the needed responses and treatments in these instances. It does still remain, however, that extremely high levels of reliable and effective production of proper medical treatments based on mAbs platforms will be necessary to ensure product to address broad disease application or broad civilian exposure in the case of WMD release or even during unexpected virus spread.

Again, as alluded to above, typical mAbs production methods involve mammalian cell reactors. Certainly, such an approach has been successfully employed for predicted supply requirements involving expected disease outbreaks, thus allowing for long timelines for scale-up to meet the overall supply needed for such large-scale treatments. Unfortunately, these types of mammalian cultures, whether small- or large-scale in effect, are not well suited for rapid response and varying scale production. Capital requirements associated with cell growth, space requirements, and even use amortization are rather expensive and the costs for such expenses are rather difficult to achieve. Upstream facilities and slow product turnaround cycles for mammalian based production processes are overly expensive and the lack of definitive understanding (even with expected outbreaks) as to the actual need for such resultant treatment products (vaccines, etc.) has hampered attempts to receive suitable funding (in excess of $500M, typically) for such facilities. Additionally, the long-term development process for new mAb products, particularly in terms of response to outbreaks of broader strains and/or new virus species, and the uncertainty surrounding such possible situations, has not led to any further incentives for investment in updated facilities and/or production processes. Cell line optimization, process adaptation, and requisite scale up requirements, at least, can lead to long-duration monoclonal antibody-based construct development (18-24 hours or longer, for instance), thus not only increasing the time and resources needed for such activities, but the uncertainty in terms of actual achievement of suitable treatments after such a time has passed. Furthermore, the prior mammalian-based mAbs production methods (e.g., within CHO or NSO cells) exhibit suspect and/or insufficient antibody dependent cellular cytotoxicity (ADCC) activity to potently counter rapidly replicating and pervasive pathogens (such as Ebola, for instance). Such ADCC is primarily due core fucose residues present on N-glycans thereby reducing the affinity of such compounds to the FcγRIII receptor responsible for ADCC signaling. Thus, there exists a need to undertake either expensive and uncertain glycan engineering for such mammalian-based products, or the payment of potentially high royalty rates to utilize other processes merely to attempt to modify these base structures sufficiently to ensure overall effectiveness and safety for mammalian treatment subjects. These "extra" significant production costs thus contribute to already high levels that, so far, have led to the majority of research investment to avoid certain niche clinical applications and suspect WMD challenges. These limitations thus demand new, more scalable, responsive and efficacious production strategy.

As it is, the current applications followed within the monoclonal antibody industry have, again, been primarily mammalian-based and, as alluded to above, also concern individualized purification procedures for specific antibody structures. Indeed, typically it requires up to 9 months to optimize a mammalian cell line for monoclonal antibody production. The steps may differ for different approaches, but they require the introduction of at least two different gene constructs for expression into a cell, including genes encoding the two antibody chains plus non-antibiotic selectable markers. Such genes are transfected into cells separately or jointly, and then selected for cell lines that contain both gene constructs and further express a fully assembled, two-chain, monoclonal antibody product. Following selection of expressing lines, the resultant cell lines must be compared for production of monoclonal antibody productivity and often undergo further selection for increased antibody production through gene duplication strategies using methotrexate selection that identifies cells with the highest number of dihydrofolate reductase or other selectable marker genes. These methods require analysis of many separate production cell lines and detailed screening for production capability as measured by amount of antibody per cell, typically, in a culture, for example. Following selection of optimally expressing cell lines, the lines must be optimized for culture conditions, growth characteristics, buffers, nutrients and other variables as well. The overall development process required to produce an antibody in mammalian cells is thus, as alluded to above, rather complicated to manage due to many cell lines to compare, optimize and stabilize, at least. Management of these variables of cell and production conditions requires time, scale, and expense to achieve a final, optimized cell line, too. Further, mammalian cell production requires sequential scaling of cultures from a single Master or Working Cell Bank of 1 mL or similar volume, to 10 mL, 100 mL, 1,000 mL all to subsequently seed the next sequential volume production container. Each seeding process puts cultures at risk for contamination with advantageous agents due to length of culture and the seeding process. The seeding and scale up process for full volume production takes time and a high level of expertise before production occurs. The requirement of quick-time production, in reaction to, for instance, WMD threats, unforeseen disease pandemics, and thus the need for multiple antibodies in a single product, and, furthermore the parallel comparisons of antibodies in such situations, are made very difficult due to the time, repeatable processing, and overall complexity needed to derive an optimal expression clone for each antibody, as well as the scalable requirements of sequential seeding for full volume production. Although many varied purification systems have been developed for mammalian cells (Kelley, MAbs. 2009 September-October; 1(5): 443-452; Shukla, et al., Journal of Chromatography B, 848 (2007) 28-39; Shukla, et al., 2010. Trends in Biotechnology Vol. 28 No. 5. pp. 253-261; Liu et al., 2010. MAbs. 2010 September-October; 2(5): 480-499.), each requires virus inactivation and virus filtration or removal steps that are not required for plant-based systems since they lack viruses that infected mammalian cells.

Thus, to avoid the limitations and potential pitfalls of mammalian-based mAbs production methods and products, there exists a significant need to provide an effective standardized plant-based antibody production and purification method that avoids the complexity of the time consuming process to derive optimal cell lines, optimize culture conditions, manage complex processes for scale up production just to achieve a single antibody and virus inactivation and removal steps, let alone a number of candidates required to optimize a product that may require multi-product content or different product comparison for protection or therapy against a WMD threat or another type of disease (Whaley et al., 2011. Human Vaccines 7:3, 349-356.). Standardized plant-antibody production methodologies are typically dependent of generation of transgenic plant lines that require 6-9 months to derive, and up to three years to generate sufficient seed for full-scale production. The utilization of virus vectors shortens such production time lines (Whaley et al., 2011), but each production process followed in such instances is typically conducted much like mammalian cell production activities (basically undertaking the utilization of highly tailored production and purification processes for each antibody (Ko and Koprowski, Virus Research 111 (2005) 93-100; Jain et al., 2011; Asian journal of Pharmacy and Life Science, Vol. 1(1), January-March and references therein), which thus requires high specificity and, as noted above, increased chances of off-quality batches). The trial and error process to optimize expression processes, production conditions, and purification procedures in such traditional method are time-consuming and expensive. Furthermore, although these highly optimized and tailored processes may yield optimal production levels, the time and resources required, as well as the overall complexity of such processes to produce therapies involving more than a single antibody or rapid product production required for WMD and other like threats, are far too high for economical and efficient operations. In such production methods, there exists a significant need, therefore, to permit repetitive utilization of regulatory compliant formulations, buffers, etc., while still effectuating an acceptable purification result, and all through the reliance upon a plant-based resource. To date, however, there is lacking any such method within the monoclonal antibody production/purification industry.

ADVANTAGES AND BRIEF SUMMARY OF THE INVENTION

One significant advantage of the inventive method is that the standardized capability of such a purification protocol saves development/testing costs, resources, and time since the same purification process may be applied for each monoclonal antibody production scheme. Another distinct advantage of this method is that the same equipment and raw materials, buffers etc. may be applied for the purification of each target monoclonal antibody, thereby substantially reducing, if not eliminating, the need for extra testing, supplier approvals, regulation compliance actions, etc., for the purpose of producing any such target antibody. Yet another advantage of this inventive method is that such plant-based purified antibody structures/formulations do not require any virus inactivation, removal, and/or validation studies during production and/or from one project to the next as opposed to typical mammalian-based materials. Still another advantage thereof is that the utilization of such a standardized purification method is that man-power requirements may be drastically reduced with repetitive process steps of the same amounts and types of reagents, buffers, exchange columns, etc. A further advantage is the uniformity of purification results from such a standardized method, thereby also providing for reliable product quality. A further advantage herein is the ability to develop effective and reliable regulatory compliant (such as in terms of US FDA and/or EMA standards) antibody materials through master cell banks and master seed banks through such a unique plant-based (*Agrobacterium*) manufacturing protocol.

Accordingly, this invention encompasses a method of purifying monoclonal antibodies, said method including the steps of:

a) harvesting monoclonal antibody sources from a source organism, b) extracting said antibodies from said source organism and clarifying the structure thereof;

c) processing said extracted and clarified antibodies through a series of chromatography separation procedures, i) wherein a first procedure effectuates the initial total antibody removal from said clarified extract, ii) wherein said second procedure separates and permits collection of full-length antibody structures along with removal of host cell contaminations, and iii) wherein said third procedure allows for fractional collection of different size antibody structures and final polishing of host cell contaminants; and d) collecting the resultant monoclonal antibody formulations and storing the same for utilization as a bulk drug substance. The invention also encompasses a method wherein said source organism is a plant, wherein said harvesting step includes seed production and plant germination sub-steps followed by the inducement of transient gene expressions to form a specific protein associated with a desired monoclonal antibody, and then the growth of the resultant plant including the desired monoclonal source. Upon harvesting, then, the "raw" antibody is provided in a form that is then subjected to the necessary purification procedures broadly outlined above and more succinctly described herein. Such a method that provides the necessary methodology for the production and purification of any type of monoclonal antibody in suitable form for introduction within a medicament is also encompassed herein. Additionally, the monoclonal antibodies to which the invention pertains are preferably, though not necessarily, immunoglobulin (IgG) antibodies.

Furthermore, the invention also encompasses an antibody intermediate product that is free from mammalian virus particles, whether active or inactive (defined as prior to a Protein A purification step, for instance). Thus, an antibody intermediate that has not been treated with any type of virus inactivation material and exhibits reduced, if not eliminated, virus infectivity, is within such a definition. Additionally, the invention encompasses a method of providing a suitable antibody from materials provided within a regulatory compliant master cell bank, as well as a method of providing such an antibody through a master seed bank of plant strains engineered for such production purposes, as well.

Antibodies are major components of the immune system and IgG is the main antibody isotype found in blood and extracellular fluid that provides defense to infection within body tissues. In general, antibodies provide suitable sites for binding pathogens, effectively, at least to a certain extent, providing a means to prevent pathogen activity, and thus protects the body from infection. Several immune mechanisms are thought to contribute in such a manner. For instance, IgG-mediated pathogen binding, as alluded to above, immobilizes such microorganisms, binding together via agglutination. As well, such antibodies have been known to actually coat pathogen surfaces, thereby allowing phagocytic immune cells to target such locations and ingest such recognized pathogens. Furthermore, IgG activates the classical pathway of the complement system, causing pathogen elimination through the generation of a cascade of immune protein production within certain locations of the body. Additionally, it has been understood IgG also binds and neutralizes toxins within the human body, thus helping to reduce the potential for introduction of harmful secretions, etc., from such microorganisms.

IgG antibodies are typically generated in vivo within animal tissues, such as through secretion as a small-size monomer that easily perfuses tissues, particularly in response to certain proteins that are introduced within the body. The proteins effectuate reactions to increase molecule size until such structures attain a size of roughly 150 kDa and having four peptide chains. Such structures contain two identical class γ heavy chains of about 50 kDa and two identical light chains of about 25 kDa (thus exhibiting a tetrameric quaternary structure). The two heavy chains are linked to each other and to a light chain each by disulfide bonds and the resulting tetramer has two identical halves, forming a Y-like shape. Thus, these radiating top Y ends contains identical antigen binding sites, allowing for highly effective reaction with the surfaces of viruses, bacteria, fungi, and other like pathogens. When removed from source organisms for the introduction, ultimately, within pharmaceutical preparations (and the like) for delivery within a human body, such structures include with them a number of potentially deleterious extraneous compounds. For instance, certain proteins remain bound (to a certain extent, at least) to such antibody surfaces; combined with other biochemical structures, these undesirable extras could bind to the open antibody antigen reactive sites, thus reducing the effectiveness and viability of such immune system components.

Typically, animal-based antibody sources have been widely utilized for such purposes with potential problems in that mammalian viruses may be latent within such initial materials and passed on to the resultant antibody products. As alluded to above, plant-based sources are highly desirable though such resultant antibodies are often provided with unwanted compounds contained therein and/or therewith (such as host cell proteins, host cell DNA, endotoxins, and the like). The need exists to thus overcome these potential problems with a uniform approach to purify such desirable plant-based antibody products.

Without any intention of limiting the type of plant strains available for this overall system, one particular plant strain, an engineered *Nicotiana benthamiana* (Nb) type, has shown effectiveness in terms of the inventive production method for plant-based mAbs. Such strains, for instance, have allowed generation of not only effective mAbs products, but those with highly homogenous mammalian glycans (Whaley et al., 2011). Thus, in addition to speed and scalability benefits, it has been determined that such an overall platform also accords products that drastically reduce, if not eliminate, any safety concerns about plant-specific immunogenicity. Further, such plant-derived mAbs have proven to be more potent and efficacious against, as examples, mouse-based Ebola virus and NHPs than those produced in CHO systems. This has, in turn, led to a reduced amount of mAb required to treat such a particular disease strain, thereby possibly permitting a significant improvement for such disease protections in the future. In addition to potency benefits, as noted above, this system offers significant cost savings (for both costs for construction of a manufacturing facility as well as cost of goods manufactured) compared to traditional mammalian cell culture-based manufacturing procedures.

Additionally, and as noted above, there currently exist myriad purification techniques targeted primarily to specific types of antibodies in relation to glycosylation structures. The necessity of properly extracting and separating out such highly prized immune system boosting materials requires potentially costly and highly involved methods for such a purpose. The variety, then, of reactants, buffers, etc., that allow for very quick (and presumably effective) purification results for certain antibody structures, at least, has invariably led to repeated testing, compliance, and other like requirements to permit usage of such purified antibodies exposed to myriad chemical reactants, etc., when introduced within the drug substance marketplace. The basic contact of such biochemical structures with any number and type of buffers, reactants, etc., for such purification purposes could create non-uniform results over a large range of production samples, which, in turn, could deleteriously effect target patients.

The inventive method, however, as noted previously, overcomes these distinct problems. The plant-based process first allows for greater uniformity and reliability in terms of the source organism(s) involved. Introduction of certain antibody generating DNA and/or RNA, and the like, within plant organisms invariably facilitates repetitive seed germination and growth, and, in particular, allows for uniformity in terms of the straightforward reaction of cellular components to generate the desired antibody structures. Thus, once produced, the resultant antibodies may then be extracted and clarified in a filtering process to provide a rough filtrate for further purification. This pre-purification step basically entails the harvesting of tissue samples (such as plant tissues including agro-infiltrated cells) through the utilization of a proper buffer exposed to source organism tissue. The resultant biomass is then treated with a suitable antibody extraction formulation (such as a mixture of tris hydroxymethylaminomethane, referred to commonly as Tris-Base, ascorbic acid, and ethylenediaminetetraacetic acid, known as EDTA). Cellulosic fibers (from plant biomass) can be removed physically, leaving a resultant plant extract of antibody-laden liquid. This extract is then clarified through a filtration step (such as with diatomaceous earth, as an example) and a subsequent filter press step. The resultant filter press cake is then collected and washed with a suitable buffer.

From this initial upstream process, including seed germination, agro-infiltration, organism growth, sample extraction, and antibody sample clarification, the resultant collected samples are then subjected to the multi-step purification process platform. It is this multi-step purification approach coupled with an extraction buffer step and the utilization of a filter press step that has contributed the primary beneficial results of this invention. In essence, the overall procedure actually includes a series of targeted treatments of the produced antibodies so as react with and/or remove broad types of extraneous components from the target antibody(ies). The main steps involve the utilization of at least three types of columns, including one affinity column, one ion exchange column, and one multimodal column for removal of certain classes of extraneous compounds. A first column includes a suitable resin having affinity for antibody structures (such as, one non-limiting example, mAb SelectSure), packed to a suitable bed height (from about 8 to 15 cm, preferably about 10 cm), and capable of holding from 8 to 15 mg per mL of resin preferably about 10 mg per mL). A certain amount of Tris-HCl is then utilized to equilibrate the column prior to antibody extract being introduced therein. One the extract sample introduction is completed, the loaded resin is then washed with successive mixtures of Tris-containing liquids, one with a NaCl or Arginine additive, another later one without such a salt.

This initial removal step is then followed by antibody elution with a 3.0 pH weak acid (such as 100 mM acetic acid/200 mM arginine mixture). The resultant eluent is then immediately neutralized by a Tris formulation that is set to a specific pH level below the isoelectric point for the target antibody eluted from the plant biomass sample.

The neutralized eluent sample is then introduced within an ion exchange column, including, again, as one non-limiting example, Capto Q packed to a bed height from about 6-12 cm (preferably about 8 cm) that has been equilibrated with a certain molarity and amount of (4-(2-hydroxyethyl)-1-piperazine ethane-sulfonic acid) (referred to commonly as HEPES) or a suitable Tris formulation. The antibody eluent is then diluted with water to facilitate injection and loading on the Capto Q column (again, for at least about 2 minutes residence time). The desired antibody structure (in full-length state) is found within the flow-through fraction thereof and collected. Further washing of the column results in the collection (in separate fractions) of antibody fragments (rather than total-length structures), endotoxins, and other types of molecules that deleteriously effect the capabilities of the collected antibodies.

Lastly, a polishing step is then undertaken through the utilization of, as one non-limiting example, a ceramic hydroxyapatite particle (80 micron) (multimodal) column packed to a bed height of between 8 and 21 cm (preferably about 10 cm). The column is prepared to permit a target 5-15 mg antibody binding per mL of CHT resin as well as measuring a conductivity of less than 10 ms/cm. Furthermore, the column is prepared through neutralization and equilibration through a formulation of pH 6.8 sodium phosphate. Thereafter, the full-length antibody sample is loaded to the column at a minimum 2 minute residence time and then washed with sodium phosphate. As above, the antibody sample is then eluted from the column over a certain gradient between sodium phosphate alone and the same with sodium chloride present. Fractions are then removed within specific mAU intervals, with low molecular weight fragments presents within the lower mAU portions. Monomeric antibody samples are present greater than 100 mAU fractions. Thereafter, the column is stripped through exposure to sodium phosphate with the purified target antibody aggregates within the strip fraction. Such a CHT elution is preferably performed through a pressurized membrane system, with the resultant antibody sample eluent then introduced in a concentrated formulation and diafiltered against a buffer solution (including, for instance, sodium citrate or histidine, amino acid (such as glycine, as one non-limiting example), sugar, and a suitable nonionic surfactant, at a near-neutral pH (such as from 5.5-6.0). This diafiltered sampled is then concentrated to a desired level and collected and stored at a suitably low temperature (between, for instance −70 and −80° C.). This collected and stored sample is thus of the desired antibody structure for utilization as a bulk drug substance.

The invention described herein thus provides not only the capability of mAbs through a plant-based platform, but also a standardized antibody purification platform that may be utilized for the production of a wide selection of different mAbs. The method steps themselves that accord such a one-size-fits-all approach have heretofore not been combined in a single purification scheme, but have been relegated to single steps for a variety of different purification/reaction processes. The important consideration is the utilization of the sequential purification steps that utilize specific column types to effectuate the necessary initial total antibody removal from a clarified plant extract, then separation of full-length antibody structures, and finally collection of different fractions of antibody fragments as desired for selection of specific structures as a bulk drug substance source.

Such a method is described in greater detail below.

DETAILED DESCRIPTION OF THE DRAWINGS AND PREFERRED EMBODIMENTS

Figure 1:
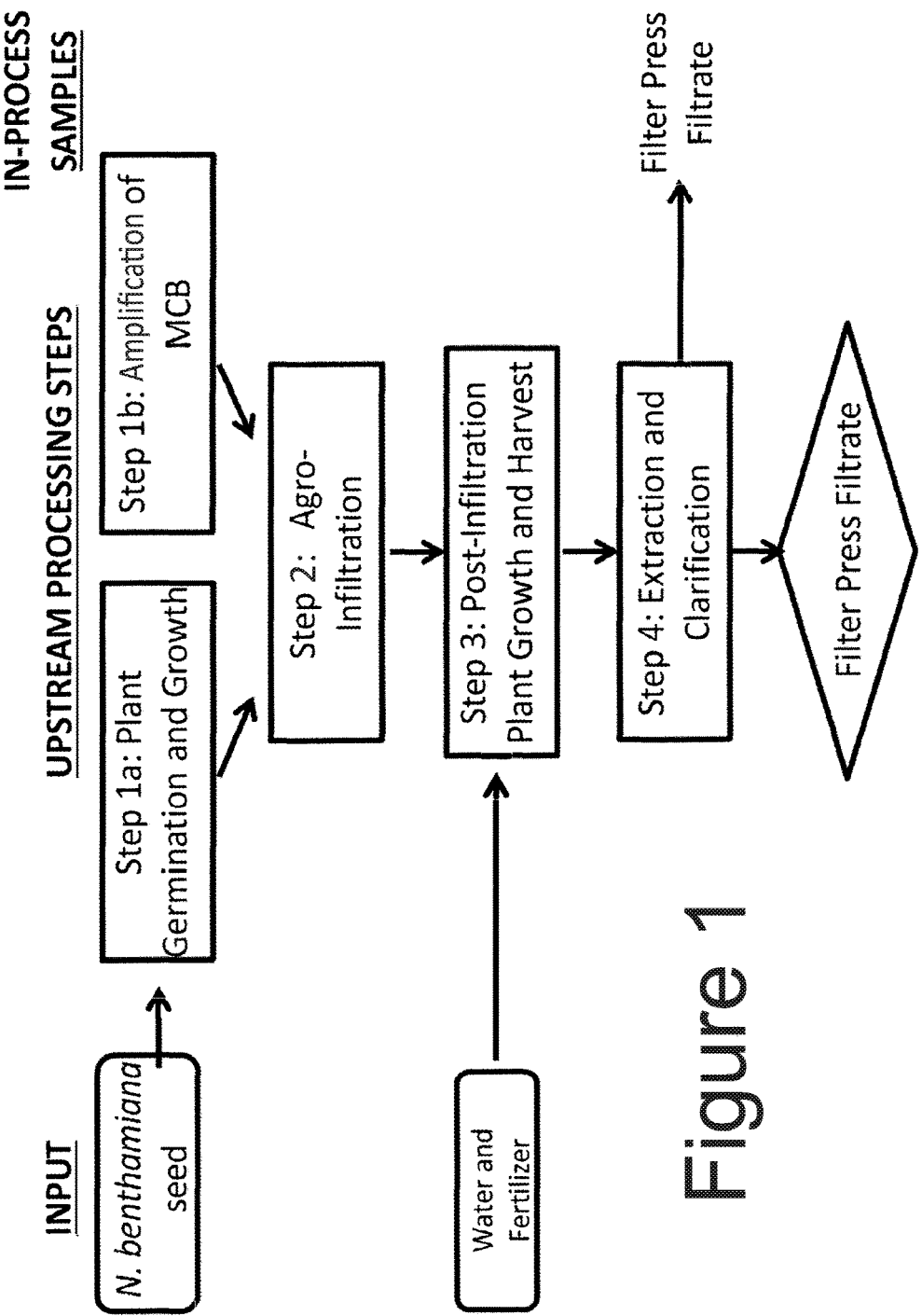
FIG. 1 is a flow chart of upstream processing steps for the ultimate extraction of antibody products from a source organism, from germination, protein initiation, organism growth, antibody harvest, and extraction thereof.

All the features of this invention and its preferred embodiments will be described in full detail in connection with the following illustrative, but not limiting, drawings and examples.

Broadly considered, the method involves the production of monoclonal antibodies through a plant-based system with purification techniques to allow for resultant materials that may be employed in a variety of different medical treatments. This method will thus be explained in terms of an initial vector expression system, a subsequent host production system, and a final harvest, extraction and purification system all in relation to specific plant strains discussed as potentially preferred, and non-limiting examples, for such an overall platform.

Vector System

The initial system employs a transient minimal virus-based system (a virus that does not encode the full complement of genes to independently complete the full virus movement process) launched by infiltration of plants with *Agrobacterium* strains. This basic process is known in the art, and has proven versatile with demonstrated expression of numerous heterologous proteins, including cytokines, interferon, bacterial and viral antigens, growth hormone, vaccine antigens, single chain antibodies and monoclonal antibodies (mAbs) at levels of 100 mg to in excess of 1 gram (g) of total soluble protein per kilogram (kg) of fresh biomass tissue.

In one aspect of the known infiltration process, a plasmid containing the virus vector is transfected into *Agrobacterium* strains, which are grown and used to infiltrate whole plants, resulting in simultaneous infection of all leaves of the plant with the vector. The *Agrobacterium* delivers the transfer region (or, T-DNA) to the plant cell nucleus where plant polymerases produce the infectious virus vector transcript which, after transit to the cytoplasm, replicates to high levels independently producing movement proteins for extension of the infection to neighboring cells and production of high levels of recombinant protein throughout infiltrated leaves.

The vectors for mAb expression in this situation are built from two different plant virus genomes. For this particular example, tobamovirus-based vectors such as tobacco mosaic tobamovirus, including turnip vein clearing tobamovirus, or other related virus genome, and potexviruses, such as potato virus X and other related genomes can be used due to their non-competitive nature in plants, as non-limiting examples. The cDNAs of the virus replicons, encoding all the genes required for virus RNA replication, are launched via an Agro-infiltration process that initially introduces the virus vectors, carried by the introduced *Agrobacterium* bacterial vector, to many cells throughout the subject transfected plant. The vector then is "activated" by transcription from the transfer or T-DNA region to produce the virus RNA in vivo and transits it to the cytoplasm for RNA amplification via virus-encoded proteins. The vectors encode requisite proteins for cell to cell movement, including the movement (30K) protein from tobamovirus-based vectors and the triple block products and coat protein for potexvirus-based vectors. These proteins allow movement of the virus vector genome locally within an inoculated leaf resulting in the majority of cells being infected and becoming production sites for the desired protein product in as few as 5-10 days. Aerial parts of the plant are then harvested generally by 6-8 days post inoculation (dpi) and extracted for the desired product. The virus coat protein is required for systemic movement through natural vascular movement, thus these vectors support cell to call movement but not systemic, moving from phloem source to sink tissues.

Master Cell Banking

In a mAbs production process using the inventive platform, genes for Heavy (HC) and Light (LC) antibody chains are subcloned into tobamovirus and potexvirus expression vectors present in cDNA form in *Agrobacterium* compatible T-DNA vectors. Unique T-DNA constructs are transformed into *Agrobacterium* strains and plants are inoculated with two distinct strains, containing either tobamovirus or potexvirus vectors. Different signal peptides are fused to each test HC and LC genes and comparison of expression levels and mAb assembly (detecting free HC and LC observed in non-reducing SDS-PAGE gels). Vectors showing similar HC and LC expression at similar levels and high degrees of mAb assembly are chosen for production.

In terms of Master Cell Bank (MCB) utilization, then, each antibody is treated separately with cDNAs encoding both of the heavy and light chains. Each of the antibody heavy and light chains are presented in the minimal virus expression system constructed from two non-competitive virus genomes, tobamoviruses, such as tobacco mosaic virus or related virus genome, and potexviruses, such as potatovirus X or related virus genome, present in distinct *Agrobacterium tumefaciens*-mediated transfer-DNA (T-DNA) vectors. All vector DNA plasmids are completely characterized by DNA sequence analysis. The *Agrobacterium tumefaciens* industrial strain, such as ICF320 (*A. tumefaciens* C58-derived; ΔcysKa, ΔcysKb, ΔthiGS, ΔT-DNA::lacZ, Rif®), is used for the antibody production system. Such a strain has further been either phenotypically and sequence characterized for auxotrophies, LacZ, and rifampicin resistance.

Vector plasmids with T-DNAs, containing each antibody chain, were individually transformed into electrocompetent *Agrobacterium tumefaciens* strain such as ICF320. Two Master Cell Banks (MCBs) for antibodies were provided therefrom under cGMP compliance according to appropriate production batch records or standard operating procedures. Specifically, these MCBs were produced for each mAb in the *Agrobacterium tumefaciens* strains. Bacterial stock solutions from the two ICF320 cell lines were scaled up in Animal Product Free-Luria-Bernani (APF LB) microbial medium, dispensed in 0.5 ml aliquots of a cell/glycerol mixture into sterile, individually labeled and individually numbered 1.7 ml Microcentrifuge tubes and stored at −80° C. as the Master Cell Bank. Such Banks are thus provided in suitable format for a proper disposition log to be utilized to track usage of each MCB glycerol stock tube, thereby permitting MCB testing and utilization under sets of identity, purity and viability assays. From these MCBs, then, mAb production is conducted for amplification and infiltration as needed and as compliant in terms of regulatory requirements (FDA and EMA agencies, for example). Working Cell Banks (WCB) are thus generated from MCBs through direct amplification, aliquoting and storing in frozen form. The WCBs were analyzed similarly to the MCB procedure described above.

| | Working Cell Bank Listings | |
|---|---|---|
| Document # | Document Title | Comments |
| BR-VDT-001 | Preparation of Master Agrobacterium Bank | Cloning, selection, and production of MCB |
| BR-VDT-002 | Preparation of Electrocompetent ICF320 | Cells used for cloning vector into Agro to produce MCB |
| BR-VDT-003 | Colony Morphology (Agro ICF320) | Phenotypic evaluation of ICF320 |

Working Cell Bank Listings

| Document # | Document Title | Comments |
| --- | --- | --- |
| BR-VDT-004 | Auxothrophy Testing for Agro ICF320 | Test ICF320 auxotrophy with and without thiamine and cysteine in media |
| BR-VDT-005 | Antibiotic Sensitivity Testing for Agrobacterium | Selection based on growth response to presence of various antibiotics |
| BR-VDT-006 | Microbial Viability Analysis | Colorimetric based microbial viability assay using water-soluble tetrazolium salts |
| BR-VDT-007 | Prep of Plasmid DNA from Agrobacterium Master Cell Bank and Sequencing analysis | DNA sequencing of mAb component insert |
| BR-VDT-008 | Agrobacterium Master Cell Bank Expression Testing: Production on N. benthamiana plants | Western Blot analysis of mAb extracted from plants |
| BR-VDT-001 | Preparation of Master Agrobacterium Bank | Cloning, selection, and production of MCB |

Host and Master Seed Banking

Thus, for monoclonal antibody production, as one non-limiting example of a plant-based platform, Nicotiana benthamiana plants (Nb) or modified Nb lines, are used for mAb production. Other plant strains, as well as other Nb strains, are certain possible and thus can be developed through genetic engineering, mutagenesis or selective breeding to enhance mAb production to exhibit particular added or eliminated molecular, metabolic, chemical modification, protein accumulation or other agricultural traits. Qualification of Nb seeds is based on seed size, germination frequency and defined storage conditions and expiration dating.

In terms of Seed Bank (SB) generation, the particular Nb strain is grown for seed-mother plants. Seed stocks were produced and qualified using appropriate production batch records and/or standard operating procedures. In summary, parent plants for seed were grown in fully contained greenhouses. Temperature, photoperiod, fertility, and diseases were regulated to optimize floral development and ultimately seed production. Mature seed pods were collected after approximately four months of growth. After cleaning, seed from each parent plant was tested for germination, growth and emergence, morphological results, correct phenotype via ELISA and immunostrip testing, testing for presence of the NPTII selectable market, and Western blot analysis for absence of undesired glycosylation on expressed proteins. Germination tests were conducted on all progeny seed lots. Acceptable seed production capacity exceeds 30 kg/year with approximately 3 kg required for a 10 kg production of mAb. Seeds were pelletized using a light-weight binder optimized for Nb strains, as well. Such pellets are colored to allow for identification and validation of each host for further utilization within the mAb production methods described herein.

The plants from these seed banks were then tested for germination. All plant growth compartments were fully contained and controlled to bio-safety level two for the greenhouses and level three for the growth rooms. The biomass production facility was operated in a quality controlled environment with computer control of temperature, light and humidity. Standard operating procedures (SOP) and batch production records (BPR) were also utilized for each production run to maintain an integrated quality system.

For test expression or non-regulated mAbs, lots were produced, and informal cell banks for each HC and LC expression vectors were maintained. However, for industrial-scale transfection of plants using Agrobacterium or the use of the mAb for regulated purposes, it was useful to have a well-defined and well-characterized Agrobacterium strain. Therefore, an industrial strain was engineered starting from the well-known and entirely sequenced wild type Agrobacterium strain is used, such as C58. Master Cell Banks (MCB) containing the aforementioned DNA vectors were produced from fully characterized (sequence and functional testing) vectors and Agrobacterium cell lines as described above. Bacterial stocks housing these vectors were diluted routinely 1,000-fold to obtain adequate compositions for infiltration, as well. The infiltration process was capable of being staged at scales of a few kilograms to greater than 1,000 kg of biomass, as well, thus providing an effective scalable process.

Nb plants have been grown under many different configurations, such as plants per pot, pots per tray, size of pots and trays have been tested. Most work well. However, for optimal production, seeds were placed into a tray system that accommodates 128 plants/tray in a pre-wetted tobacco soil-less mixture using a precision needle-seeding or barrel-seeding device. A lid was then placed over the seeded trays such that the seedlings grew through a hole in the lid, separating the aerial portion of the plant from the roots materials beneath the lid. Plants germinated for up to 7 days using humidification covers, and were subsequently uncovered to permit plant growth at an average temperature of 30° C., a level at which they were maintained prior to transfection.

The aforementioned vectors were then applied by Agro-infiltration of Nb plants at optimal growing times, often 26-28 days post sowing. The trays were then manually loaded into an infiltration system using a liquid solution in reservoirs containing the Agrobacterium solution from the amplified WCBs of HC and LC expression vectors present in two distinct Agrobacterium strains. The process initiated with the culturing of Nb plants from the seed stock. A vial of each WCB Agrobacterium cell line (each containing a tobamovirus and potexvirus vector with HC and LC vectors as empirically determined) was then amplified and used to infiltrate the plants. A vacuum was applied and then released to allow entrance of the Agrobacterium solution into the interstitial spaces of the submerged plant tissues.

Thereafter, inoculation processes were undertaken via a non-limiting Programmable Logic Controlled (PLC) robotic system to infiltrate plants, as well as another non-limiting manual infiltration chamber system. Having both allows for redundant systems to consider and assess risk mitigation. Diluted *Agrobacterium* cultures were placed in an infiltration chamber and plants, present in tray units, were inverted and subjected to 23 inches of Hg vacuum for 2 minutes with a 15-17 second release back to atmospheric pressure, within a total cycle time of about 4-4.5 minutes. The plants were then allowed to dry in an inverted position before returning the plants to the growth environments. Upon completion of the vacuum cycle, plants were removed and drained and the trays were then rotated to an upright orientation and conveyed out of the infiltration chamber for transport to the controlled growth environment. Upon exit, the next set of trays was then introduced and the cycle was repeated. Plants were incubated in greenhouse or controlled growth environments for a period of time, usually between 7-10 days, depending on product-specific optimization of plant biomass and yield. The automated and manual systems utilized herein were designed to efficiently infiltrate as much 2000 kg of Nb plants in an eight-hour production cycle.

In an exemplary use of methods and steps disclosed herein, a plasmid vector was characterized and transformed into an *Agrobacterium* strain for MCB and WCB derivation and characterization. WCBs from two strains, separately containing HC and LC expression vectors, were amplified for infiltration and plants were seeded in trays with specially designed lids to permit growth while simultaneously providing a barrier for soil and root components. Upon growth attainment to appropriate size, the trays were loaded on conveyors to enter a vacuum-rated chamber. The conveyors rotated 180° and entered an infiltration chamber, at which time the plants were submerged in *Agrobacterium*-containing solution and a vacuum was applied and then released. The resultant plants were then removed from the chamber, drained of excess solution, and rotated to upright positions and subsequently transferred to greenhouses for growth and product accumulation, extraction, and purification (as described in greater detail below).

Harvest, Extraction and Production System

As shown in FIG. 1, the initial upstream processing protocol includes an alternative first step. Step 1a allows for the provision of plant germination and plant growth (with, in this specific non-limiting embodiment, the utilization of *N. benthamiana* seeds for source organism generation). Step 1b permits an amplification procedure of the desired monoclonal antibodies, leading to the infiltration thereof of such protein sources within the germinated plants in Step 2. Proper feeding and care of the infiltrated plants thus lead to Step 3 with desired plant-growth and ultimately harvesting of the monoclonal antibody infiltrated plant samples. These plant samples are removed from the source organism for antibody extraction, clarification, and purification.

Figure 2:
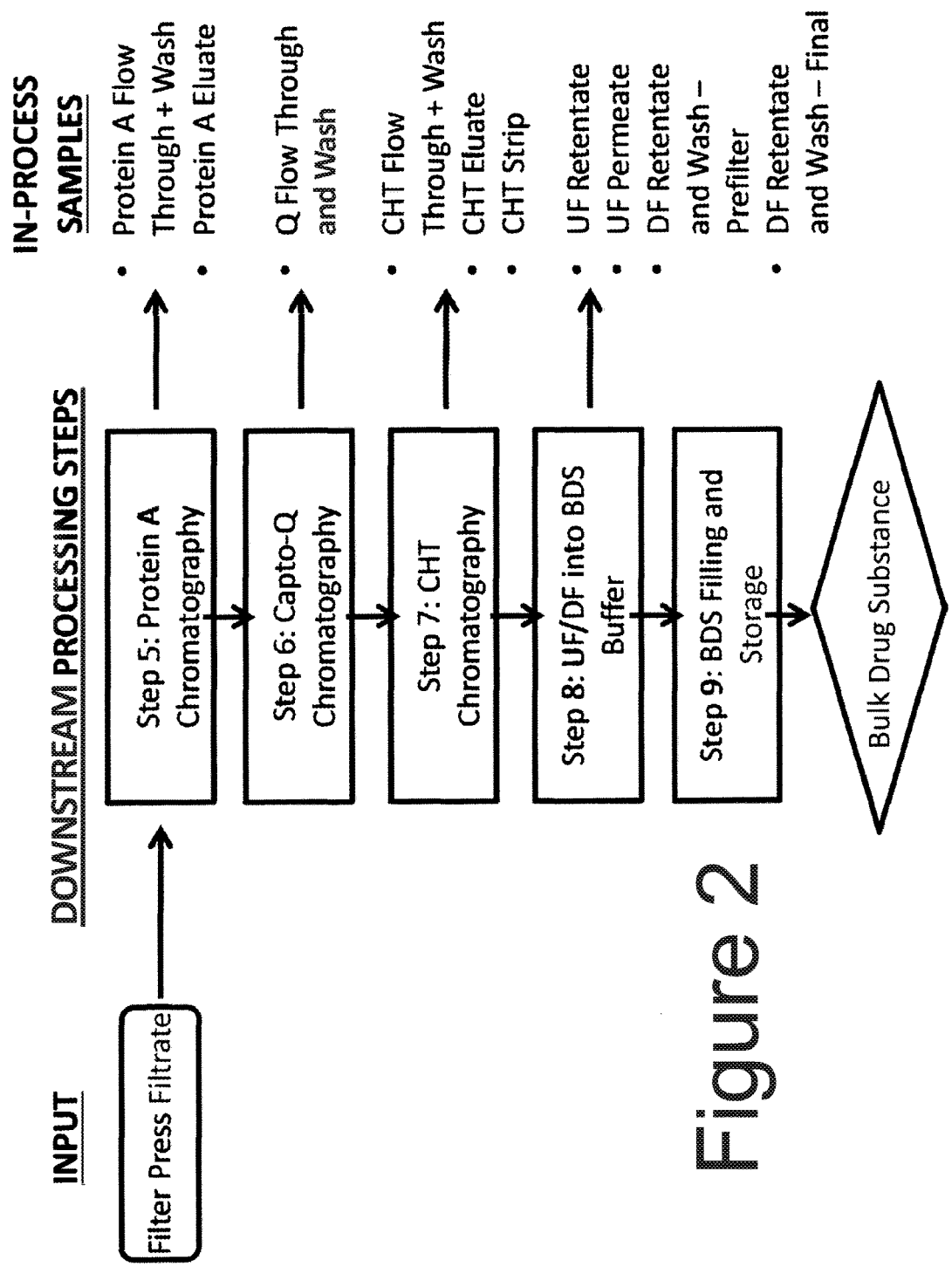
FIG. 2 is a flow chart of downstream processing steps for the purification of the extracted antibody.
Figure 3:
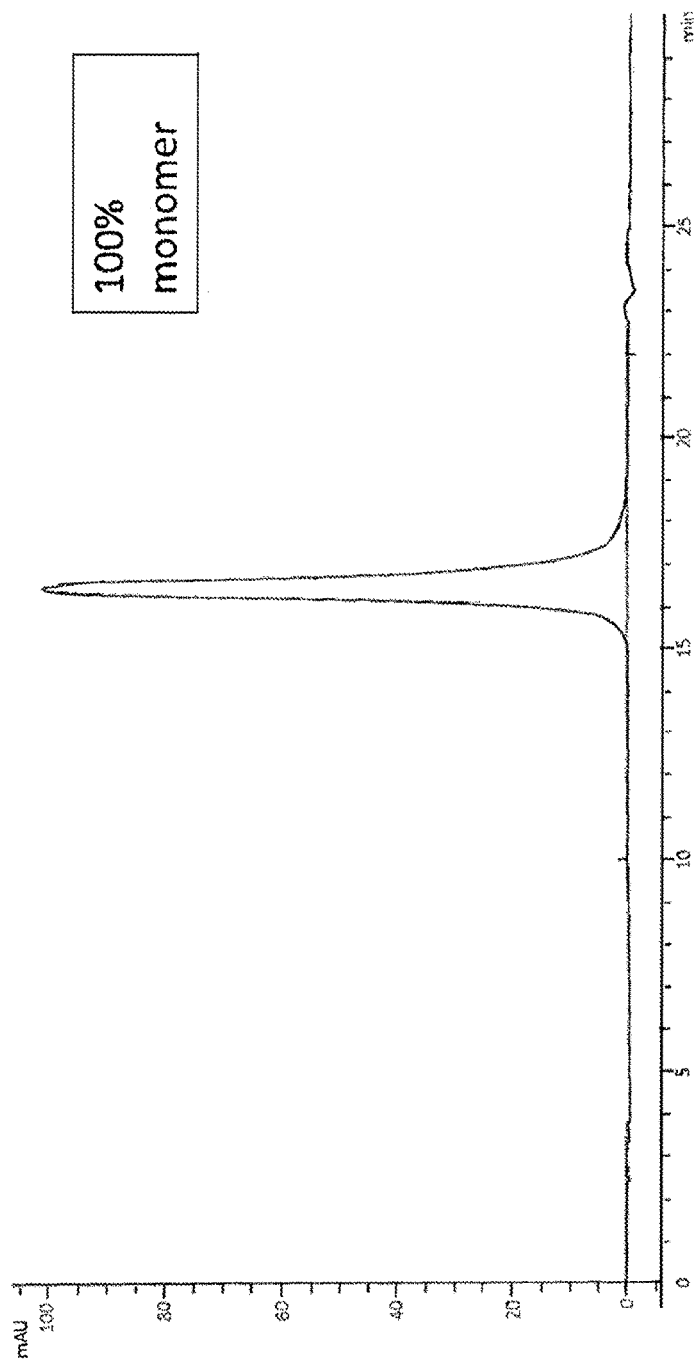
FIG. 3 is a HPLC result showing the final % of monomeric IgG with Antibody A derived from the platform process.
Figure 4:
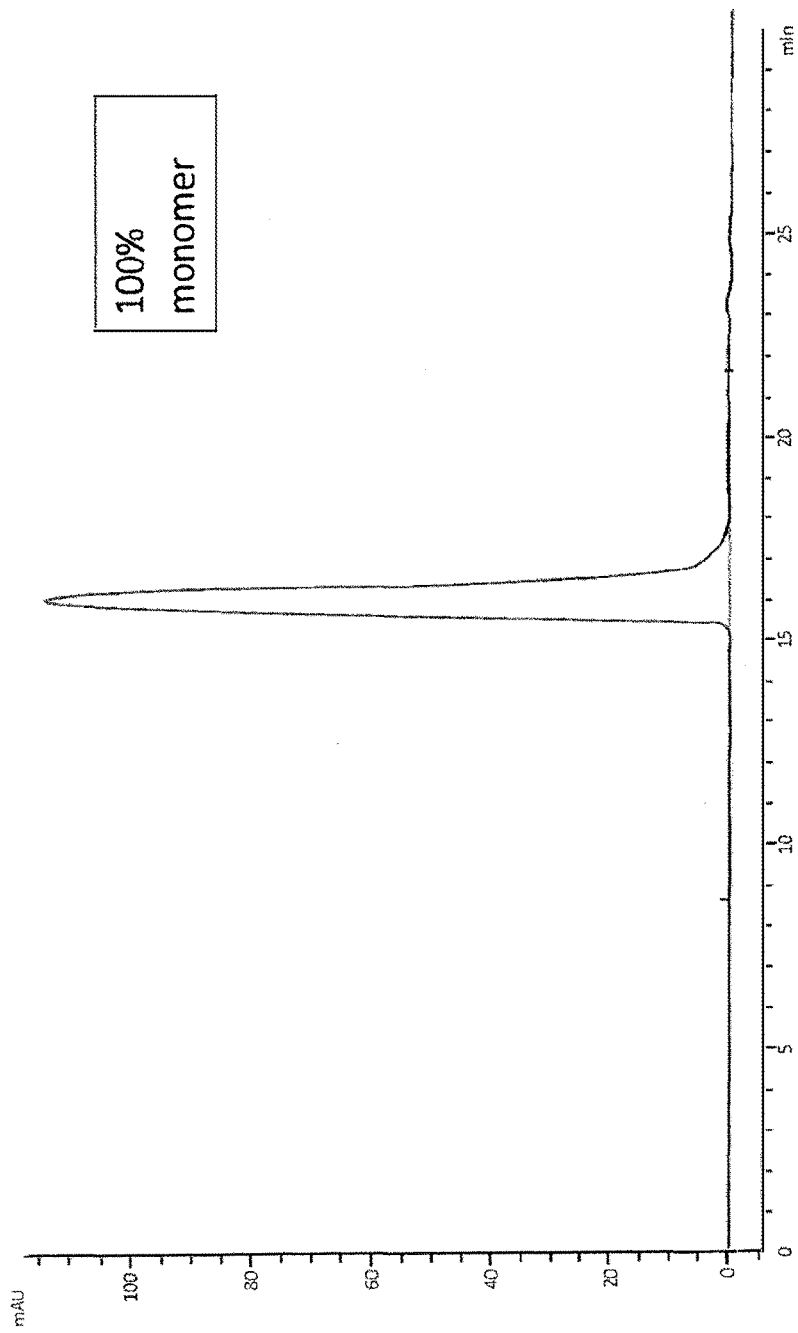
FIG. 4 is a HPLC result showing the extraction level of monomeric IgG with Antibody B derived from the platform process.
Figure 5:
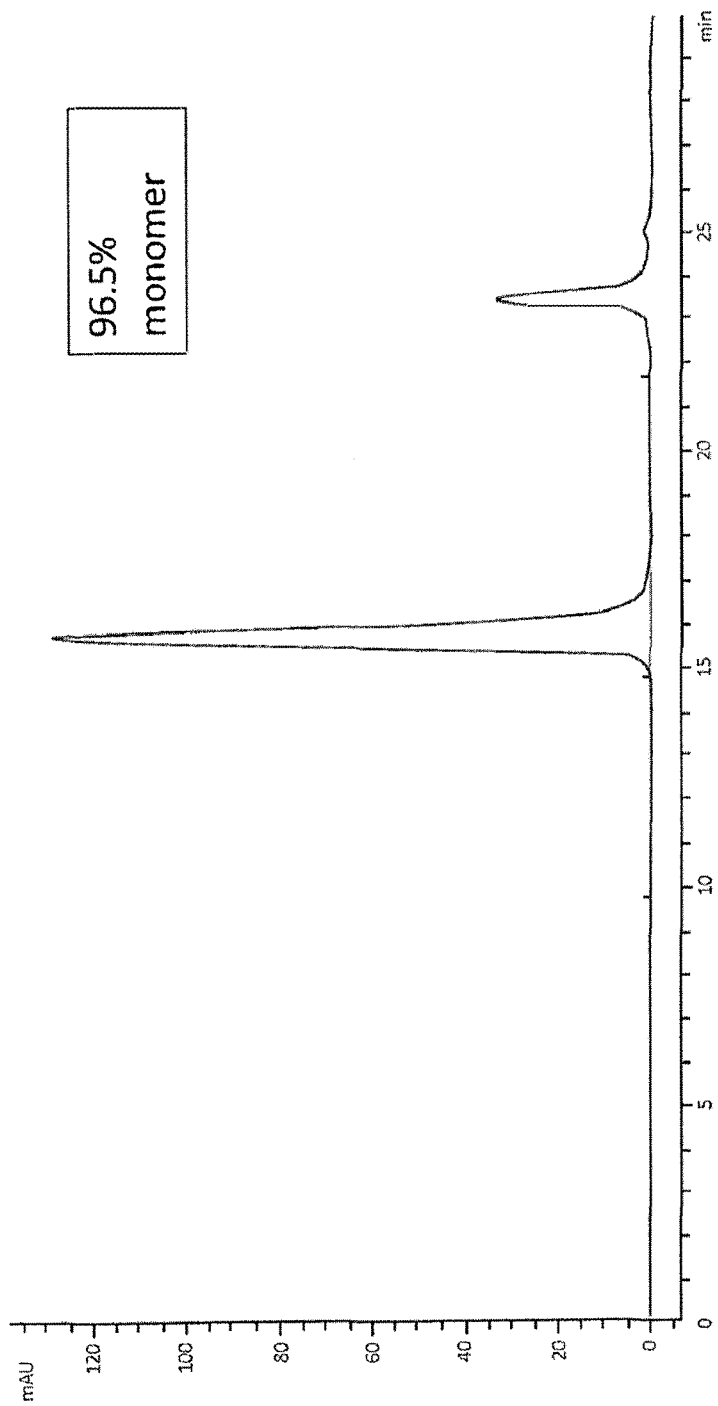
FIG. 5 is a HPLC result showing the extraction level of monomeric IgG with Antibody C derived from the platform process.
Figure 6:
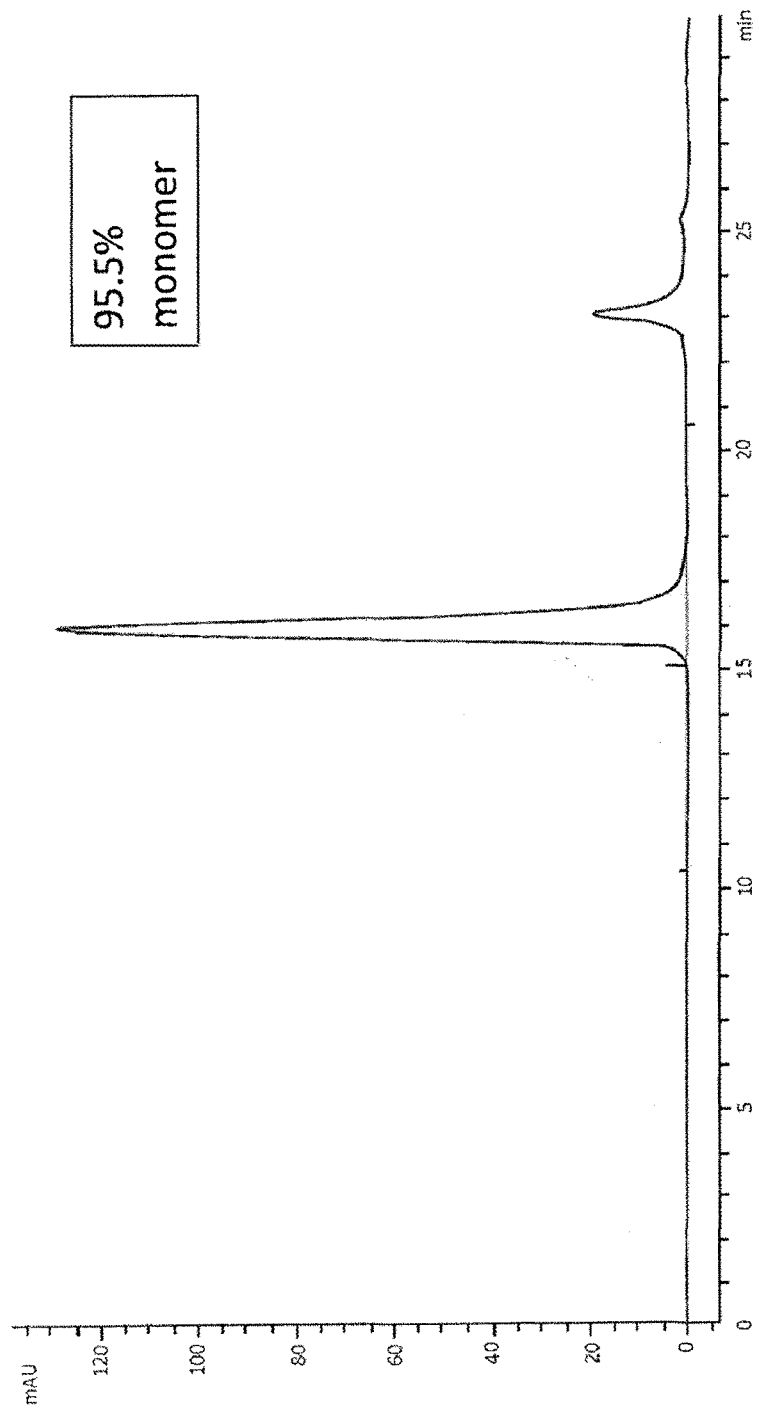
FIG. 6 is a HPLC result showing the extraction level of monomeric IgG with Antibody D derived from the platform process.
Figure 7:
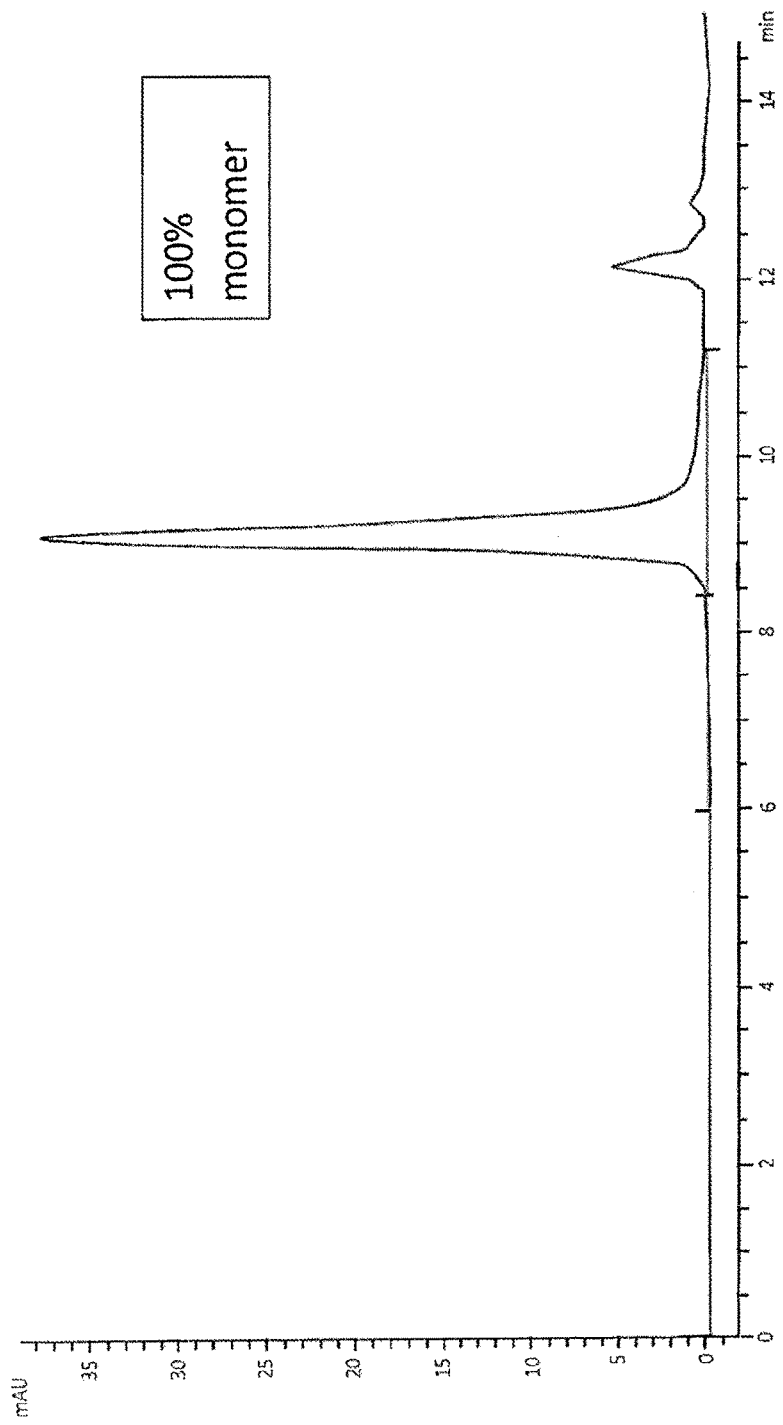
FIG. 7 is a HPLC result showing the extraction level of monomeric IgG with Antibody E derived from the platform process.

Again, as alluded to above, the antibody type that is utilized for infiltration, etc., is of any type that can be infiltrated within the target source organism. Once the plant source is then harvested, Step 4 shows the further step, first, extraction of the desired biomass from the plant sample. This is accomplished through the utilization of a suitable buffer introduced in a concentration of buffer to tissue ratio of 0.5:1. Thereafter, the target antibodies are extracted from such a plant biomass with 100 mM Tris-Base+40 mM Ascorbic Acid+1 mM EDTA, pH 8.5. Residual cellulosic plant fiber is then removed (such as through a screw press, as one example) and the resulting extract is adjusted to a pH of about 8.0 with NaOH. Clarification of such extracted antibody samples is then undertaken through the introduction of diatomaceous earth (Celpure C300) as a filter aid in an amount of about 33 grams per liter of plant (antibody-containing) extract. The extract and filter aid is then mixed for NLT 15 minutes and subsequently clarified using a plate and frame filter press packed with 0.3 micron pads (Ertel Alsop M853). Upon completion of such a depth filtration step, the resultant filter press cake is washed with the extraction buffer at 10 times the amount of Celpure C300 added initially. At this point, the filtrate sample provides the ending point of the upstream processing steps, leading to the downstream processing steps of FIG. 2. As well, the filtrate sample at this stage is free from virus particles capable of infecting mammalian cells. Such analysis for such virus particle considerations includes, as examples, photomicroscopy (since such particles are easily viewed if present), and infection assays (to test for infectivity potential of such samples using cytopathic effect or other cellular readouts). The lack of such mammalian cell infectious virus particles is due to the plant-based manufacturing schemes, thus showing a distinctive feature of this overall method compared with mammalian cell manufacturing processes that will contain infectious viruses. The particles must be inactivated and removed through added steps unique to purification schemes from mammalian cells.

The overall purification protocol is thus initiated through Step 5, termed Protein A Chromatography. In this step, a monoclonal antibody (SelectSure, from GE Life Sciences) affinity column is packed with sufficient amount of resin to generate an approximately 10 cm bed-height result. As well, this amount is generally capable of holding 10 mg of antibody per mL of resin for proper loading thereof. The column is then equilibrated with 50 mM Tris-HCl, pH 8.0 with NLT 5 CV, thus allowing for loading of the clarified plant extract thereon for a minimum residence time of 2 minutes. Upon load completion, the resin is then washed with NLT 5 CV of 50 mM Tris, pH 8.0. Subsequently, the resin is then washed with 0.5 M Arginine, pH 8.0 followed by 5 CV of 50 mM Tris, pH 8.0. The antibody thus remains bound to the column with various materials removed during these initial column washings. The collected wash eluents are then discarded. Thereafter, the remaining target antibody is eluted through introduction of 100 mM Acetic Acid+200 mM Arginine, pH 3.0, and collected at an absorbance from 100 mAU to 100 mAU. The antibody eluent is then immediately neutralized in the collection container with 1 M Tris, pH 8.0 to a pH that is at least 0.2 units below the isoelectric point for the intact antibody (here, again, preferably, IgG molecule).

The collected antibody eluent sample is then introduced within step 6, term Capto Q Chromatography. In this purification step, a Capto Q column is packed with an approximately 8 cm bed height of resin and equilibrated with 50 mM HEPES, pH 8.0 or 50 mM Tris, pH 8.0 for NLT 5 CV. The neutralized antibody eluent from Step 5 is diluted to approximately 5 ms/cm with water for injection and loaded in the negative selection mode onto the Capto Q at a minimum of a 2 minute residence time. In this step, the full-length antibody structure will be found in the flow-through fraction, rather than remaining loaded onto the column for removal of other materials therefrom. Once the fraction is then collected in this manner, the column is washed with NLT 5 CV of 50 mM Tris, pH 8.0. The column is then additionally stripped with 50 mM HEPES+3 M NaCl, pH 8.0. Unwanted antibody fragments, endotoxins, host cell proteins, and host cell DNA, at least, is found within such a strip fraction, indicating the effectiveness of such a multi-column technique.

The full-length antibody structure of Step 6 is then subjected to a final column treatment, namely Ceramic Hydroxyapatite Type II 80 micron column (CHT) Chromatography (Step 7). The column in this step is packed with an approximately 10 cm bed height of the noted resin (which equates to about 5-15 mg of antibody binding capacity per mL of resin). The CHT feed is further checked prior to loading to ensure a conductivity of less than 10 ms/cm. Subsequently, the column is then neutralized with 250 mM Sodium Phosphate for 1 CV after sanitization and then equilibrated with 5 mM Sodium Phosphate, pH 6.8 for NLT 5 CV. The Step 6 resultant antibody sample is then loaded at a minimum of 2 minute residence time onto the column. After loading, the column is washed with NLT 5 CV of 5 mM Sodium Phosphate, pH 6.8. Thereafter, the antibody is eluted over a 30 CV gradient between 5 mM Sodium Phosphate and 5 mM Sodium Phosphate+500-550 mM NaCl, pH 6.8 holding the gradient at OD280 peak max. Fractions from 20-100 mAU, as noted above, are found to contain low molecular weight fragments, and monomeric antibody samples are collected at an absorbance greater than 100 mAU. Thereafter, the column is stripped with 250 mM Sodium Phosphate for 5 CV and the undesired antibody aggregates and host cell contaminants are present as eluent within this final column strip fraction. Additionally, Step 8 involves the subjecting of the Step 7 elution fraction eluent to an ultrafiltration step (the eluent is concentrated on a 30 kDa polyethersulfone membrane to 5 mg/ml at a TMP of 7 PSI) followed by diafiltration process against 7 volumes of formulation buffer containing 20 mM Sodium Citrate, plus 10 mM Glycine, plus 8% Sucrose, plus 0.001% Tween80, at a from pH 5.5 to 6.0, or 20 mM L-Histidine, plus 4% sucrose, plus 100 mM NaCl, or 200 mM Arginine, plus 0.001% tween80, at a pH 6.0. After the 7-volume diafiltration, the antibody is then introduced within Step 9, which involves further concentration of the ultimate collected antibody sample to 20 mg/ml and then sterile filtration and storage of the collected concentrated sample at a temperature between −70° C. and −80° C. This stored antibody sample, provided in purified state, is thus suitable as a bulk drug substance on demand.

This complete method, and particularly the downstream processing steps including the inventive multi-column purification procedures can thus be implemented in relation to any type of antibody harvested from a suitable plant-based source organism. Plant sources are, as noted above, particularly viable due to the reliability and uniformity of plant samples in relation to agro-infiltration methods of DNA and thus antibody generation therein. Additionally, the inventive multi-column processing steps include accepted reagents, buffers, and the like, that do not require any further investigation, testing, etc., for regulatory compliance purposes. The resultant antibodies will thus not be subject to regulatory scrutiny prior to acceptance and utilization within drug substances.

Thus, this one-size-fits-all approach accords a highly effective, efficient, and important development within the antibody production industry.

FIGS. 3-7 show the result of implementing this uniform purification method for different antibody sources. Antibodies B-E were purified utilizing the exact process/reagents noted above, whereas Antibody A was purified in a slightly different manner wherein the protein A elution buffer was acetic acid only (no arginine) and the CHT buffers used 10 mM Sodium Phosphate in place of the 5 mM Sodium Phosphate. These Antibodies (A-E) were also all derived from Nb plants that had the Xylose and Fucose sugar transferase genes knocked-down. The resultant purified Antibodies A-E were thus analyzed through HPLC to determine the level of IgG monomer provided through such a production and purification protocol. The graphs within the above-referenced FIGS. 3-7 show that as high as 100% IgG assembled monomer is possible through the inventive purification method (and the lowest levels provided thereby were 96.5% and 95.5%, respectively for Antibodies C and D; incredibly high levels for purified or unpurified materials).

Additionally, resultant products were also analyzed for further characteristics and benefits in terms of overall capabilities for efficiency, reliability, and scalability results. To that end, testing of the final products were conducted according in accordance with a protocol prepared for each product manufactured describing the criteria for acceptance and actual release test results detailing each antibody product's purity, identity, and potency. Such protocols further allows for modular testing of mAb products which reduces the costs and time for testing through use of similar methodologies, similar qualifications, similar outsourced laboratories and similar personnel training.

Such a protocol basically involved nine different produced and purified antibodies generated through the above-described plant-based production method, including the modular nature thereof. The qualities of the genes and vectors (all pertaining to an IgG1 isotope and a k Light Chain Class material) tested for overall robustness within the inventive production process are shown in Table 1, below. The targeted diseases for such resultant monoclonal antibodies, as well as the pertinent Heavy and Light Chain Vector differences are presented as well.

TABLE 1

Tested Monoclonal Antibodies

| | | Vector Type | |
|---|---|---|---|
| mAb | Target Disease | Heavy Chain | Light Chain |
| c19F1 | Anti-SEB | A625 | A1082 |
| cPB10 | Anti-Ricin | A1030 | A1036 |
| huPB10 | Anti-Ricin | A1427 | A1433 |
| ac1H3 | Anti-Ebola | A1225 | A1227 |
| c2G4 | Anti-Ebola | A1234 | A1236 |
| c4G7 | Anti-Ebola | A1249 | A1251 |
| c4G7m1 | Anti-Ebola | A1466 | A1253 |
| c13c6-Fr1MB | Anti-Ebola | A329 | A326 |
| RSV | Respiratory Syncytial Virus | A762 | A1002 |
| Trastuzumab | Breast Cancer | pPFC0011C* | pPFC0011C* |

Table 2, below, thus provides more in-depth measurements showing the consistency and reliability of the scalable production method and purification process for such mAbs. The individual purification steps are outlined with indications of the undertaking of specific sub-steps within the overall protocol, as well. The resultant measurements for mAb viability (in terms of endotoxin EU/mg calculations) with regard to such overall processing steps are also provided (Legend: For Protein A conditions—AW=Arginine Wash, yes or no; AA/ARg.=100 mM Acetic Acid with 200 mM Arginine, added at a pH of 3.0, yes or no; RT=time, in minutes, kept on the column; For Capto Q conditions—Feed pH=feed pH within 0.2 units of molecule pI, yes or no; Feed C'tivity=feed conductivity measured at 5 mS/cm, yes or no, or as modified; For CHT conditions—Buffers=presence of buffers at 6.8 pH, yes or no; E'tion=elution of product with 500 mM NaCl, yes or no, or as modified; ET G'dient=30CV elution gradient holding at peak max for collected materials, yes or no; UF/DF conditions—CT=Concentration Target of 20 mg/mL, yes or no, or as modified; FB=presence of formulation buffer of 20 mM citrate and 10 mM glycine and 8% sucrose and 0.001% Polysorbate 80, at a pH of 6.5, yes or no).

TABLE 2

Measured Results For mAbs Production Process

| mAb | Protein A | | | Capto Q | |
|---|---|---|---|---|---|
| | AW | AA/Arg. | RT | Feed pH | Conductivity |
| c19F1 | No | No | 2 min | No | No (<10 mS/cm) |
| cPB10 | No | Yes | 2 min | No | No (<10 mS/cm) |
| huPB10a | Yes | Yes | 5 min | Yes | Yes |
| c1H3 | Yes | Yes | 2 min | Yes | Yes |
| c2G4 | Yes | Yes | 5 min | Yes | Yes |
| c4G7 | Yes | Yes | 5 min | Yes | Yes |
| c4G7m1 | Yes | Yes | 5 min | Yes | Yes |
| c13C6-Fr1 | Yes | Yes | 5 min | Yes | Yes |
| MB-RSV | Yes | Yes | 15-20 min | No | Yes |
| Trastuzumab | No | Yes | 0 min | Yes | Yes |

| mAb | CHT | | | UF/DF | | |
|---|---|---|---|---|---|---|
| | Buffer | E'tion | ET Grad. | CT | FB | Endotoxin EU/mg |
| c19F1 | Yes | 550 mM | Yes | Yes | Yes | 1.03 |
| cPB10 | Yes | 550 mM | Yes | Yes | Yes | 2.10 |
| huPB10a | Yes | Yes | Yes | Yes | Yes | 0.27 |
| c1H3 | Yes | Yes | Yes | 40 mg/mL | No | 0.067 |
| c2G4 | Yes | Yes | Yes | Yes | No | 0.01 |
| c4G7 | Yes | Yes | Yes | Yes | No | 0.007 |
| c4G7m1 | Yes | Yes | Yes | Yes | No | — |
| c13C6-Fr1 | Yes | Yes | Yes | Yes | No | 0.104 (and 0.45) |
| MB-RSV | Yes | 250 mM NaPO$_4$ | Yes | 100 mg/mL | Yes | — |
| Trastuzumab | No | 550 mM | No | 1 mg/mL | No | 0.4 |

Thus, the overall production and purification methods described above, particularly utilizing the plant-based mAbs products is shown. Such a purification method is described herein utilizing the affinity column, ion-exchange column, and multimodal column extractions followed by the necessary buffer extract method and specific filter press procedures accords a (nearly substantially) uniform process to generate a highly purified antibody product for direct incorporation within a desired medical formulation. The present system thus offers a unique solution to these prior (mammalian-based) manufacturing problems due to its speed and scalability, at least. Furthermore, such an overall protocol provides the ability to utilize reliable starting materials that do not require any additives to inactivate mammalian cell infective viruses, let alone any degree of potentially problematic virus infectivity levels, as well as the ability to avoid any need for centrifugation for purification of the resultant mAbs themselves, thus providing a streamlined, effective overall production method at substantially lower cost, higher reliability, and uniform in basic operation for the generation of multiple types of viable mAbs. In this manner, there is available a transition of a lead vaccine candidate from expression construct to acceptable amounts of product within an acceptable time frame (about 6 months). In comparison with mammalian-based production schemes, these mAbs (plant-based) are significantly better in terms of reliability, time to product, and scalability. The costs, then, needed for such scalability, speed, and reliability are well below those typically required for mammalian-based mAbs production methods.

Figure 8:
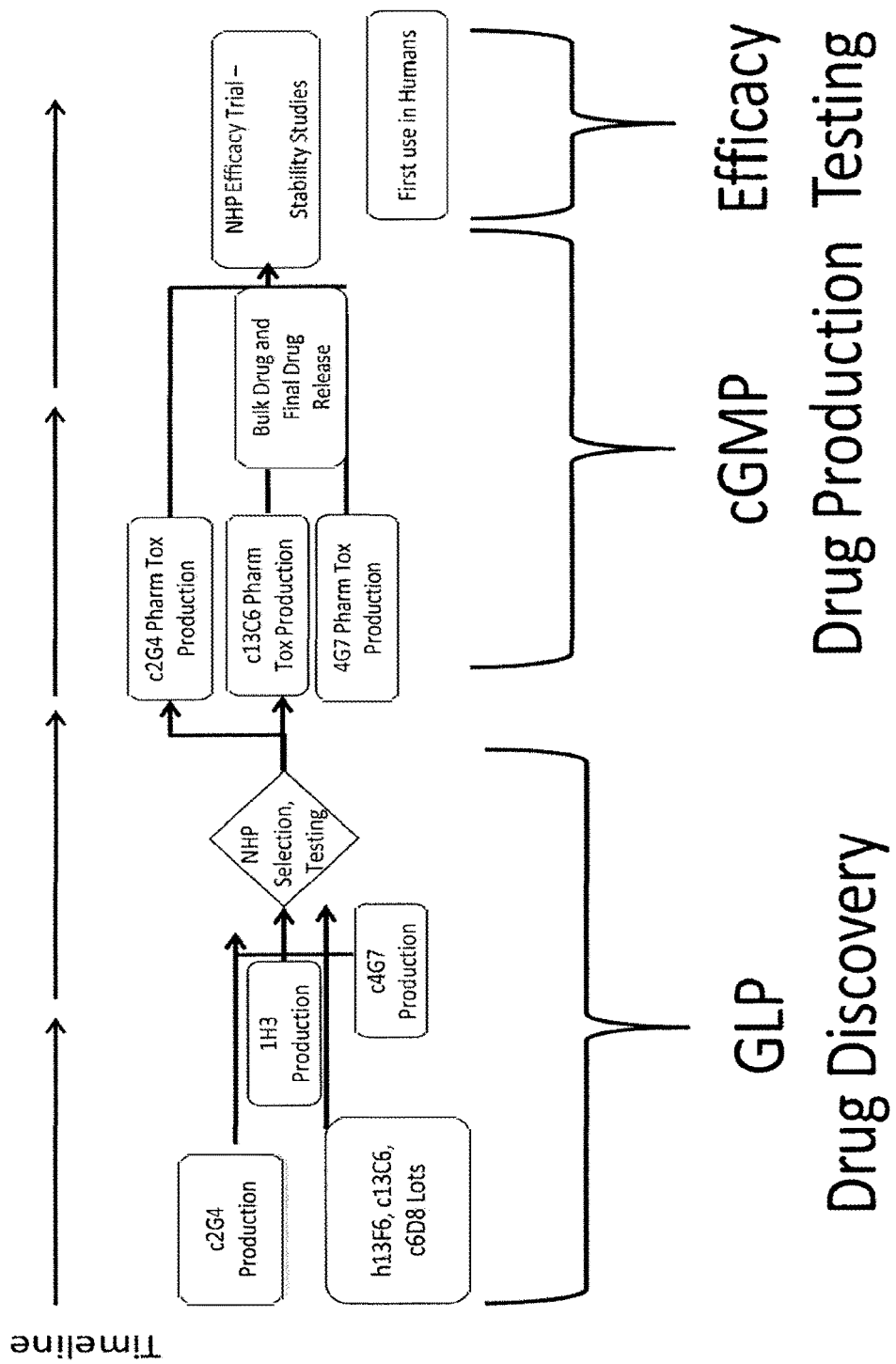
FIG. 8 is a diagram providing a potentially preferred method of production of an Ebola virus treatment antibody through the inventive production and purification protocol.

The strength of this invention can be illustrated in the development of a product used as a therapeutic to treat Ebola infection. FIG. 8 shows a production diagram of the process. To derive this product, three previously studied antibodies developed as the MB-003 product (c6D8, c13C6-FR1, and h13F6) were tested in various combinations with three additional antibodies (c2G4, 1H3, c4G7). The initial MB-003 mAbs were subjected to in vitro characterization. Characterizations thereof demonstrated that the c6D8 and c13C6 mAbs had in vitro neutralization activity ($IC_{80}$=6.25 µg/ml), whereas h13F6 did not. In this instance, c13C6 and c6D8 recognized linear epitopes, while c13C6 recognized a conformational epitope and cross-reacted with other Ebola viruses (Sudan and Ivory Coast). This cross-reactivity was confirmed through Biacore analysis; c13C6 binds to recombinant Sudan GP with approximately one-fourth the affinity it displays for Zaire GP (as determined by Biacore).

The MB-003 mAbs were previous developed, including the generation of expression constructs, plant infiltrations, protein accumulation, and purification. These lots were available for testing with each of the NML antibodies in all possible three-antibody permutations. To generate test lots for the three NML mAbs, the platform development including construct development, Master Cell Banking, process and protein production process began with c2G4 mAb, 1H3 a few months thereafter, and c4G7 a year thereafter. Each of these antibodies were provided with the already produced h13F6, c6D8 and c13C6 mAbs, for in vitro testing (as described above) and in vivo testing for efficacy using non-human primate tests with Ebola challenge. These tests, comparing antibodies in three-antibody combinations, resulted in the selection of the following product content mAbs: c13C6-FR1, c4G7 and c2G4. This selection initiated a new production platform development for c13C6-FR1. The completion of the three production platforms for c13C6-FR1, c4G7 and c2G4 mAbs were then completed and full Pharm-tox production Campaigns were initiated with Master Cell Banks thereafter and completed three months later. This work resulted in three antibody lots for product formulation and Pharm-Tox Stability, as well as Sentinel DP finish and fill lots for later testing. These activities showed the overall ability to generate four production platform systems in 6 months for four distinct mAbs allowing for proper in vitro and in vivo tests to select antibody contents (and perform possible additional studies). This utilization of the same platform system for each antibody provided both speed and effectiveness to produce highly purified and highly efficacious mAbs for such in vivo testing, thus showing the ability to not only provide effective results in this manner through a single production/purification protocol, but also the ability to do so from a Master Cell Bank (and Master Seed Bank, for that matter) for an overall streamlined methodology.

It should be understood that various modifications within the scope of this invention can be made by one of ordinary skill in the art without departing from the spirit thereof. It is therefore wished that this invention be defined by the scope of the appended claims as broadly as the prior art will permit, and in view of the specification if need be.

What is claimed is:

1. A method of purifying monoclonal antibodies, following their production in a source organism, said method including the steps of:
   a) harvesting monoclonal antibody sources from the source organism;
   b) extracting said antibodies from said source organism and clarifying the antibodies;
   c) processing said extracted and clarified antibodies through a series of chromatography separation procedures, i) wherein a first procedure includes an affinity column from which the target antibody is eluted with an arginine-containing acidic buffer to form an eluent containing full-length monomeric antibody structures, ii) wherein a second procedure includes an ion-exchange column for separating and collecting the full-length antibody monomeric structures from the eluent of step "c(i)", and iii) wherein a third procedure includes a multimodal column from which the target antibody is eluted over a gradient established between at least one salt, during which the monomeric antibody structures are collected;
   d) subjecting the collected antibody structures from step "c(iii)" to a buffer extraction step;
   e) filtering said collected antibody structure fraction through a multiple filter press operation; and
   f) collecting the resultant filtered monoclonal antibody formulations and storing the same for utilization as a bulk drug substance;
   wherein extracting antibodies from said source organism in step "b" is performed with an extraction formulation comprising an alkaline buffer, an antioxidant and a chelating agent, and wherein before performing step "c(ii)" the antibody eluent of step "c(i)" is neutralized to a pH that is at least 0.2 units below the isoelectric point for the antibody.

2. The method of wherein said source organism is a plant.

3. The method of claim 2 wherein said harvesting step includes seed production and plant germination sub-steps followed by the inducement of transient gene expressions to form a specific protein associated with a desired monoclonal antibody, and then the growth of the resultant plant including the desired monoclonal source.

4. The method of claim 1 wherein the said monoclonal antibodies are immunoglobulin (IgG) antibodies.

5. The method of claim 1 wherein said method does not require any centrifugation steps for mAb extraction.

6. The method of claim 1 wherein step involves direct loading onto said affinity column and also wherein the gradient in step "c(iii)" is established between Sodium Phosphate-Sodium Chloride and the gradient is held once an absorbance reading exceeds 100 mAU.

7. The method of claim 1, wherein monoclonal antibodies are generated from plants infiltrated with *Agrobacterium* lines separately containing expression constructs for each monoclonal antibody, one for heavy chain and the other for light chain production and wherein the method further comprises
   incubating said infiltrated plants from 5 to 10 days post-infiltration to generate monoclonal antibody sources within source organisms present within said subject plants.

8. The method of claim 7 wherein said monoclonal antibodies are not subject to centrifugation for processing, clarifying, and/or extracting.

9. The method of claim 8 wherein said subject plants are provided from a master seed bank.

10. The method of claim 8 wherein said subject plants include *Nicotiana benthamiana* plants.

* * * * *